(12) United States Patent
Takagi

(10) Patent No.: US 11,166,694 B2
(45) Date of Patent: Nov. 9, 2021

(54) POSITIONING SUPPORT APPARATUS, RADIOGRAPHIC IMAGING SYSTEM, AND STORAGE MEDIUM

(71) Applicant: Konica Minolta, Inc., Tokyo (JP)

(72) Inventor: Tatsuya Takagi, Mitaka (JP)

(73) Assignee: KONICA MINOLTA, INC., Tokyo (JP)

( * ) Notice: Subject to any disclaimer, the term of this patent is extended or adjusted under 35 U.S.C. 154(b) by 65 days.

(21) Appl. No.: 16/830,788

(22) Filed: Mar. 26, 2020

(65) Prior Publication Data
US 2020/0315566 A1    Oct. 8, 2020

(30) Foreign Application Priority Data

Apr. 8, 2019   (JP) .............................. JP2019-073646

(51) Int. Cl.
*A61B 6/00*    (2006.01)
*A61B 6/04*    (2006.01)

(52) U.S. Cl.
CPC ............ *A61B 6/547* (2013.01); *A61B 6/0407* (2013.01); *A61B 6/461* (2013.01); *A61B 6/52* (2013.01)

(58) Field of Classification Search
CPC .......... A61B 6/04; A61B 6/0407; A61B 6/461; A61B 6/465; A61B 6/488; A61B 6/52; A61B 6/545; A61B 6/547; A61B 6/587
See application file for complete search history.

(56) References Cited

FOREIGN PATENT DOCUMENTS

| JP | H04-364834 A | 12/1992 |
|---|---|---|
| JP | 2018-143699 A | 9/2018 |

*Primary Examiner* — Dani Fox
(74) *Attorney, Agent, or Firm* — Lucas & Mercanti, LLP

(57) ABSTRACT

A positioning support apparatus includes a hardware processor. The hardware processor obtains a radiographic image of a subject taken through a radiography. Based on the obtained radiographic image, the hardware processor detects a relative positional relationship between the subject and at least one of a radiation detector and a radiation source, the positional relationship being at a time when the radiographic image is taken. The hardware processor receives a change input for simulating a change of a position of the at least one of the radiation detector and the radiation source. Based on the detected positional relationship and the received change input, the hardware processor generates a simulation-reflected image that is an image of the subject reflecting the change of the position of the at least one of the radiation detector and the radiation source. The hardware processor outputs the generated simulation-reflected image.

6 Claims, 7 Drawing Sheets

POSITIONING SUPPORT APPARATUS, RADIOGRAPHIC IMAGING SYSTEM, AND STORAGE MEDIUM

CROSS-REFERENCE TO RELATED APPLICATIONS

The entire disclosure of Japanese Patent Application No. 2019-073646 filed on Apr. 8, 2019 is incorporated herein by reference in its entirety.

BACKGROUND

1. Technological Field

The present disclosure relates to a positioning support apparatus, a radiographic imaging system, and a storage medium.

2. Description of Related Art

In taking a radiographic image of a subject, a region as a diagnosis target (diagnosis target region) in the radiographic image may be chipped or hidden under a region showing another part of the body, as a result of positional deviation of a radiation detector and/or a radiation source with respect to the position of the subject. Because such a chipped or hidden diagnosis target region makes it difficult to diagnose correctly, the position of the radiation detector and/or the radiation source with respect to the position of the subject needs to be corrected to take another images.

To deal with this, there have been proposed various techniques for supporting positioning the radiation detector and/or the radiation source.

For example, JP 2018-143699A describes a medical image capturing control device that obtains imaging conditions regarding the positioning of an imaging unit, obtains a radiographic image of a subject by controlling the imaging unit, calculates a correction amount of the imaging conditions on the basis of the obtained radiographic image, and sends notification of the calculated correction amount.

Further, JP 04-364834A describes a radiographic image reading system that determines whether or not a relative positional relationship between a subject and a radiographic image reading device is appropriate on the basis of the read radiographic image data, and outputs notification on the basis of the determination result.

SUMMARY

However, the device disclosed in JP 2018-143699A displays the correction amount in number. Thus, a user has to take another images without being sure whether or not a desired radiographic image can be actually obtained after the correction according to the correction amount provided by the device.

Further, the system disclosed in JP 04-364834A only notifies that the relative positional relationship between the subject and the device is inappropriate. Thus, even if receiving notification from the system, the user is not sure what correction should be made to obtain a desired radiographic image, and has to repeat correcting the positional relationship and taking images until the system stops outputting notification.

Objects of the present disclosure include, when the position of the radiation detector and/or the radiation source deviates with respect to the position of the subject, allowing a user to easily learn a method of correcting the deviation and determine whether or not a desired radiographic image can be obtained by the correction according to the method.

To achieve at least one of the abovementioned objects, according to an aspect of the present invention, there is provided a positioning support apparatus including a hardware processor that: obtains a radiographic image of a subject taken through a radiography; based on the obtained radiographic image, detects a relative positional relationship between the subject and at least one of a radiation detector and a radiation source, the positional relationship being at a time when the radiographic image is taken; receives a change input for simulating a change of a position of the at least one of the radiation detector and the radiation source; based on the detected positional relationship and the received change input, generates a simulation-reflected image that is an image of the subject reflecting the change of the position of the at least one of the radiation detector and the radiation source; and outputs the generated simulation-reflected image.

To achieve at least one of the abovementioned objects, according to another aspect of the present invention, there is provided a radiographic imaging system including: a radiation detector that generates a radiographic image of a subject based on a radiation received from a radiation source; a hardware processor that detects, based on the radiographic image generated by the radiation detector, a relative positional relationship between the subject and at least one of the radiation detector and the radiation source, the positional relationship being at a time when the radiographic image is taken, receives a change input for simulating a change of a position of the at least one of the radiation detector and the radiation source, based on the detected positional relationship and the received change input, generates a simulation-reflected image that is an image of the subject reflecting the change of the position of the at least one of the radiation detector and the radiation source; and a display that displays the generated simulation-reflected image.

To achieve at least one of the abovementioned objects, according to another aspect of the present invention, there is provided a non-transitory computer-readable storage medium storing a program that causes a computer to perform: obtaining that is obtaining a radiographic image of a subject taken through a radiography; relative position detecting that is detecting, based on the radiographic image obtained in the image obtaining, a relative positional relationship between the subject and at least one of a radiation detector and a radiation source, the positional relationship being at a time when the radiographic image is taken; input receiving that is receiving a change input for simulating a change of a position of the at least one of the radiation detector and the radiation source; image generating that is generating, based on the positional relationship detected in the relative position detecting and the change input received in the input receiving, a simulation-reflected image that is an image of the subject reflecting the change of the position of the at least one of the radiation detector and the radiation source; and image outputting that is outputting the simulation-reflected image generated in the image generating.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, embodiments of the present invention are described with reference to the drawings. However, the scope of the invention is not limited to the disclosed embodiments.

First Embodiment

A first embodiment of the present invention is explained.
[Radiographic Imaging System]

Figure 1:
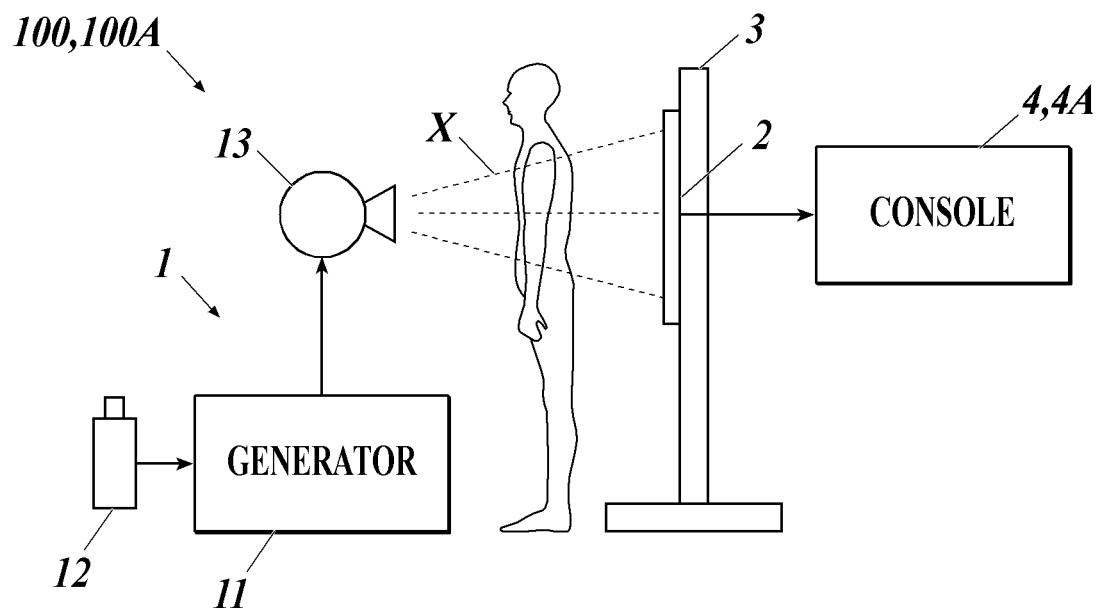
FIG. 1 is a schematic view of a radiographic imaging system according to a first (second) embodiment of the present invention.

First, a schematic configuration of a radiographic imaging system 100 in this embodiment is described. FIG. 1 is a schematic view of the radiographic imaging system 100.

Reference numerals in parentheses in FIG. 1 are used in a second embodiment to be described later.

The radiographic imaging system 100 in this embodiment includes a radiation generator 1, a radiation detector 2, an imaging stand 3, and a console 4.

The radiation generator 1, the radiation detector 2, and the console 4 are connected to each other through a communication network N or the like.

The radiographic imaging system 100 may be connectable to the hospital information system (HIS), the radiology information system (RIS), the picture archiving and communication system (PACS), and/or image analysis apparatuses, although they are not illustrated.

The radiation generator 1 include a generator 11, an irradiation instruction switch 12, and a radiation source 13 (tubular lamp).

In response to the irradiation instruction switch 12 being operated, the generator 11 applies, to the radiation source 13, a voltage corresponding to preset imaging conditions (for example, conditions concerning a subject S, such as an imaging position, an imaging direction, and a physical characteristic of the subject, and conditions concerning irradiation, such as tube voltage, tube current, irradiation time, and current exposure time product (mAs)).

When the generator 11 applies the voltage to the radiation source 13, the radiation source 13 emits radiation (e.g. X-rays) having a dose corresponding to the applied voltage.

The radiation source 13 is movable in X-axis direction (irradiation direction), Y-axis direction (height direction), and Z-axis direction (horizontal direction perpendicular to the irradiation direction), and rotatable on a shaft parallel to Y-axis and on a shaft parallel to Z-axis (i.e. the irradiation direction can be changed).

The radiation generator 1 configured as described above generates radiation X (e.g. X-rays) in a way corresponding to radiographic images to be taken (still images or movies).

The radiation generator 1 may be installed in an imaging room, or the radiation generator 1, the console 4, and so forth may constitute a movable instrument carriage.

The radiation detector 2 includes: radiation detection elements that generate, in response to being irradiated, charges corresponding to the dose of the radiation X; a sensor substrate in which pixels having switch elements that store/release charges are arranged two-dimensionally (in a matrix); a scanning circuit that switches on/off of each switch element; a reading circuit that reads out, as an signal, an amount of charges released by each pixel; a controller that generates a radiographic image on the basis of the signals read out by the reading circuit; and an outputting part that outputs data of the generated radiographic image or the like to the outside, although these are not illustrated.

When irradiated by the radiation generator 1, the radiation detector 2 generates the radiographic image corresponding to the radiation X received.

The imaging stand 3 holds the radiation detector 2.

The imaging stand 3 can move the radiation detector 2 in Y-axis and X-axis directions.

Although FIG. 1 exemplifies the imaging stand 3 for imaging a subject in a standing position, it may be for imaging a subject in a recumbent position.

The imaging stand 3 is not required when the radiation detector 2 is placed on the floor or a bed, or leaned against the wall.

The console 4 is a positioning support apparatus, and consists of a PC, a dedicated apparatus, or the like.

The console 4 can set various imaging conditions (tube voltage, tube current, irradiation time (mAs), imaging position, imaging direction, etc.) of an imaging apparatus or the like.

Details of the console 4 are described later.

Although the console 4 exemplified in FIG. 1 functions as the positioning support apparatus, the positioning support apparatus may be an individual apparatus configured separately from the console 4.

In the radiographic imaging system 100 configured as described above in this embodiment, the radiation source 13 of the radiation generator 1 and the radiation detector 2 are placed with a certain distance between them so as to face one another. The radiographic imaging system 100 takes radiographic images of the subject S by irradiating the subject S with the radiation X emitted from the radiation source 13.

When a radiographic image is taken as a still image, the radiographic imaging system 100 performs irradiation and generation of a radiographic image only one time in response to one imaging operation (pressing of the irradiation instruction switch). When radiographic images are taken as a movie, the radiographic imaging system 100 repeats pulse irradiation and generation of a frame image multiple times (e.g. 15 times per second) in response to one imaging operation.

[Console]

Figure 2:
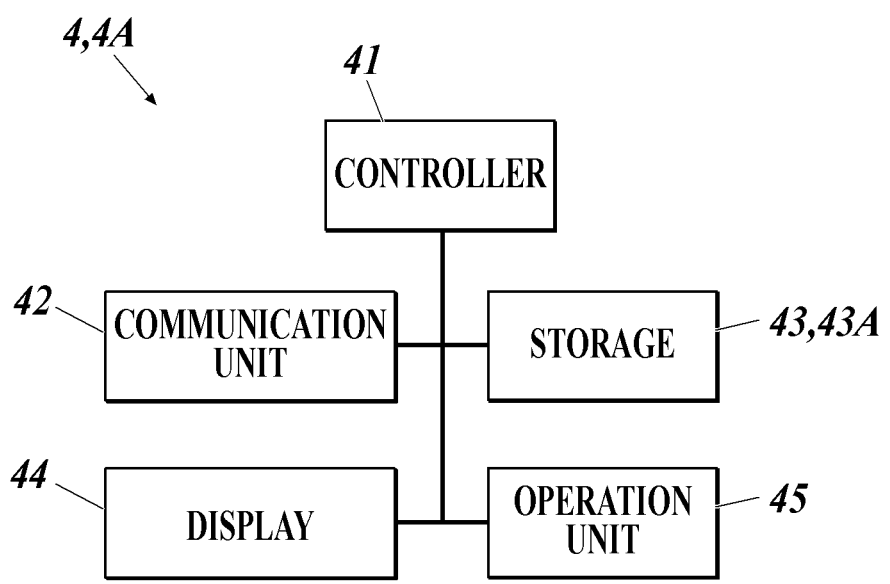
FIG. 2 is a block diagram of a console (positioning support apparatus) included in the radiographic imaging system in FIG. 1.
Figure 3:
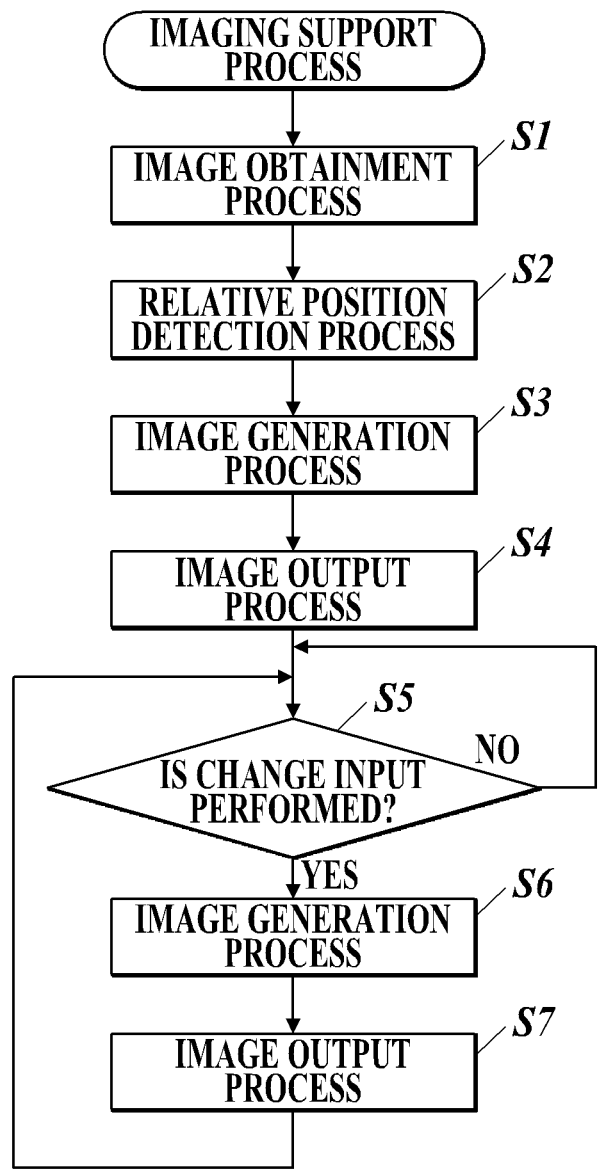
FIG. 3 is a flowchart showing an imaging support process performed by the console in the first embodiment.

Next, a detailed configuration of the console 4 included in the radiographic imaging system 100 is described. FIG. 2 is a block diagram of the console 4. FIG. 3 is a flowchart of an imaging support process performed by the console 4.

Reference numerals in parentheses in FIG. 2 are used in the second embodiment to be described later.

The console 4 in this embodiment includes, as shown in FIG. 2, a controller 41 (hardware processor), a communication unit 42, a storage 43, a display 44 (display), and an operation unit 45.

A bus or the like electrically connects the components 41 to 45 with one another.

The controller 41 includes a central processing unit (CPU) and a random access memory (RAM).

The CPU of the controller 41 reads various programs stored in the storage 43, loads the read programs into the RAM, and executes various processes in accordance with the loaded programs, thereby integrally controlling operation of each component of the console 4.

The communication unit 42 includes a communication module.

The communication unit 42 exchanges various kinds of data and/or signals with external apparatuses or the like connected to a communication network N, such as a local area network (LAN), a wide area network (WAN), or the internet.

The storage 43 includes a nonvolatile semiconductor memory and/or a hard disk.

The storage 43 stores various programs (including a program for an imaging support process to be described later) to be executed by the controller 41, parameters required for executing the programs, and so forth.

The storage 43 also stores model images required for generating a simulation-reflected image $I_2$ to be described later. The model images are images having been taken beforehand of a subject(s) who has a standard shape and in a normal condition (has no disease). Multiple model images are prepared so as to show the subject in different ways according to imaging positions and/or imaging directions.

In this embodiment, the storage 43 also stores a subject diagram(s) $D_s$ (e.g. schema image) for generating a position-reflected diagram $D_1$ to be described later. Only one subject diagram $D_s$ showing the whole body of a subject may be prepared, or multiple subject diagrams $D_s$ each showing a part of a subject (e.g. chest part, leg part) may be prepared.

The display 44 includes a monitor, such as a liquid crystal display (LCD) or a cathode ray tube (CRT), to display images.

The display 44 displays various images and so forth in accordance with control signals input from the controller 41.

The operation unit 45 includes: a keyboard including cursor keys, numerical keys, and various function keys; a pointing device, such as a mouse; and a touchscreen superposed on the surface of the display 44. The operation unit 45 outputs, to the controller 41, control signals corresponding to an operation performed by a user.

The console 4 configured as described above performs, for example, an imaging support process as shown in FIG. 3 when a certain condition(s) is met.

Examples of a certain condition include conditions: (i) that the console 4 be on, (ii) that the console 4 be connected to the communication network N, (iii) that the operation unit 45 receive a certain operation to start the imaging support process, and (iv) that the communication unit 42 receive a certain control signal from other apparatuses.

In the imaging support process, the controller 41 firstly performs an image obtainment process (Step S1). In the image obtainment process, the controller 41 obtains a radiographic image $I_1$ of a subject S taken through radiography.

Although data of the radiographic image $I_1$ is received through the communication unit 42 in this embodiment, the data may be firstly stored in a storage medium and then read by the controller 41.

The radiographic image $I_1$ to obtain may be a main image that is used for diagnosis, or a pre-taken image that is taken with a low dose of radiation before a main image is taken.

The controller 41 functions as an image obtainment unit by performing the image obtainment process.

After obtaining the radiographic image $I_1$, the controller 41 performs a relative position detection process (Step S2).

In the relative position detection process, the controller 41 detects, on the basis of the obtained radiographic image $I_1$, (i) a relative positional relationship between the radiation detector 2 and the subject S and (ii) a relative positional relationship between the radiation source 13 and the subject S at the time when the radiographic image $I_1$ is taken.

The controller 41 uses information on an edge(s) of the radiographic image $I_1$ to detect the position of the radiation detector 2. That is, the controller 41 detects the position of the radiation detector 2 on the premise that the edge(s) of the radiographic image $I_1$ corresponds to the edge(s) of the radiation detector 2.

Methods of detecting the position or the irradiation direction (irradiation angle) of the radiation source 13 are not specifically limited. A method disclosed in JP 2018-143699A may be used, for example.

Further, in this embodiment, the controller 41 detects the position of an irradiated field. Methods of detecting thereof are not specifically limited, either. The position of the irradiated field is detected on the basis of the detected position or irradiation direction of the radiation source 13, the result of reading the radiographic image $I_1$, or the like.

Although the controller 41 detects both the positional relationship between the radiation detector 2 and the subject S and the relative positional relationship between the radiation source 13 and the subject S in this embodiment, the controller 41 may detect only either of them.

The controller 41 functions as a relative position detection unit by performing the relative position detection process.

After detecting the positional relationships, the controller 41 in this embodiment performs an image generation process (Step S3).

In the image generation process in Step S3, the controller 41 generates the position-reflected diagram $D_1$ by laying, on the subject diagram $D_s$ showing at least a body part corresponding to an imaging target part imaged in the obtained radiographic image $I_1$, a detector figure $F_1$ (first figure) corresponding to the radiation detector 2 and a tubular-lamp figure $F_2$ (first figure) corresponding to the radiation source 13. The detector figure $F_1$ is laid such that a positional relationship between the subject diagram $D_s$ and the detector figure $F_1$ is identical to the actual positional relationship between the subject S and the radiation detector 2, and the tubular-lamp figure $F_2$ is laid such that a positional relationship between the subject diagram $D_s$ and the tubular-lamp figure $F_2$ is identical to the actual positional relationship between the subject S and the radiation source 13, the actual positional relationships being at the time when the radiographic image $I_1$ is taken.

When the storage 43 stores multiple subject diagrams $D_s$ each showing a part of a subject, the controller 41 reads a subject diagram $D_s$ that shows a part corresponding to the imaging target part on the basis of the imaging target part and the imaging direction (e.g. front chest) included in imaging order information.

The controller 41 in this embodiment colors an irradiated-field region R in the position-reflected diagram $D_1$, the region R corresponding to the irradiated field having been irradiated when the radiographic image $I_1$ is taken.

The procedure in Step S3 is not required if the controller 41 does not output the position-reflected diagram $D_1$ in the following image output process in Step S4.

After generating the position-reflected diagram $D_1$, the controller 41 performs the image output process (Step S4).

In the image output process in Step S4, the controller 41 outputs the radiographic image $I_1$.

Figure 4:
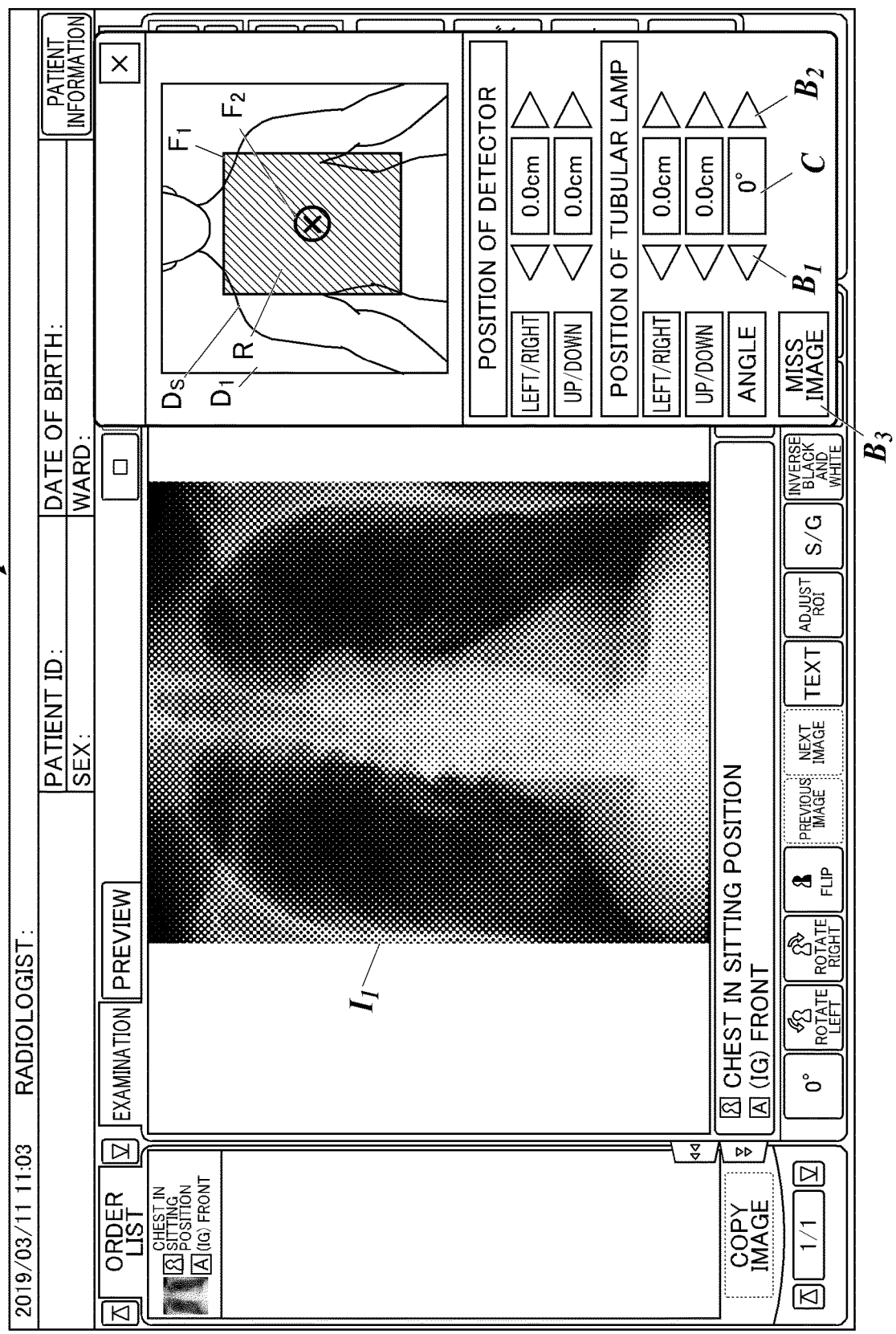
FIG. 4 is an example of a screen displayed on a display of the console in the first embodiment.

In this embodiment, the controller 41 displays the radiographic image $I_1$ and the position-reflected diagram $D_1$, which has been generated in the image generation process, on the display 44, as exemplified in FIG. 4.

Instead of displaying both the radiographic image $I_1$ and the position-reflected diagram $D_1$, the controller 41 may firstly display the radiographic image $I_1$ only, as exemplified in FIG. 5, and display the position-reflected diagram $D_1$ later in response to an operation performed by the user.

Figure 5:
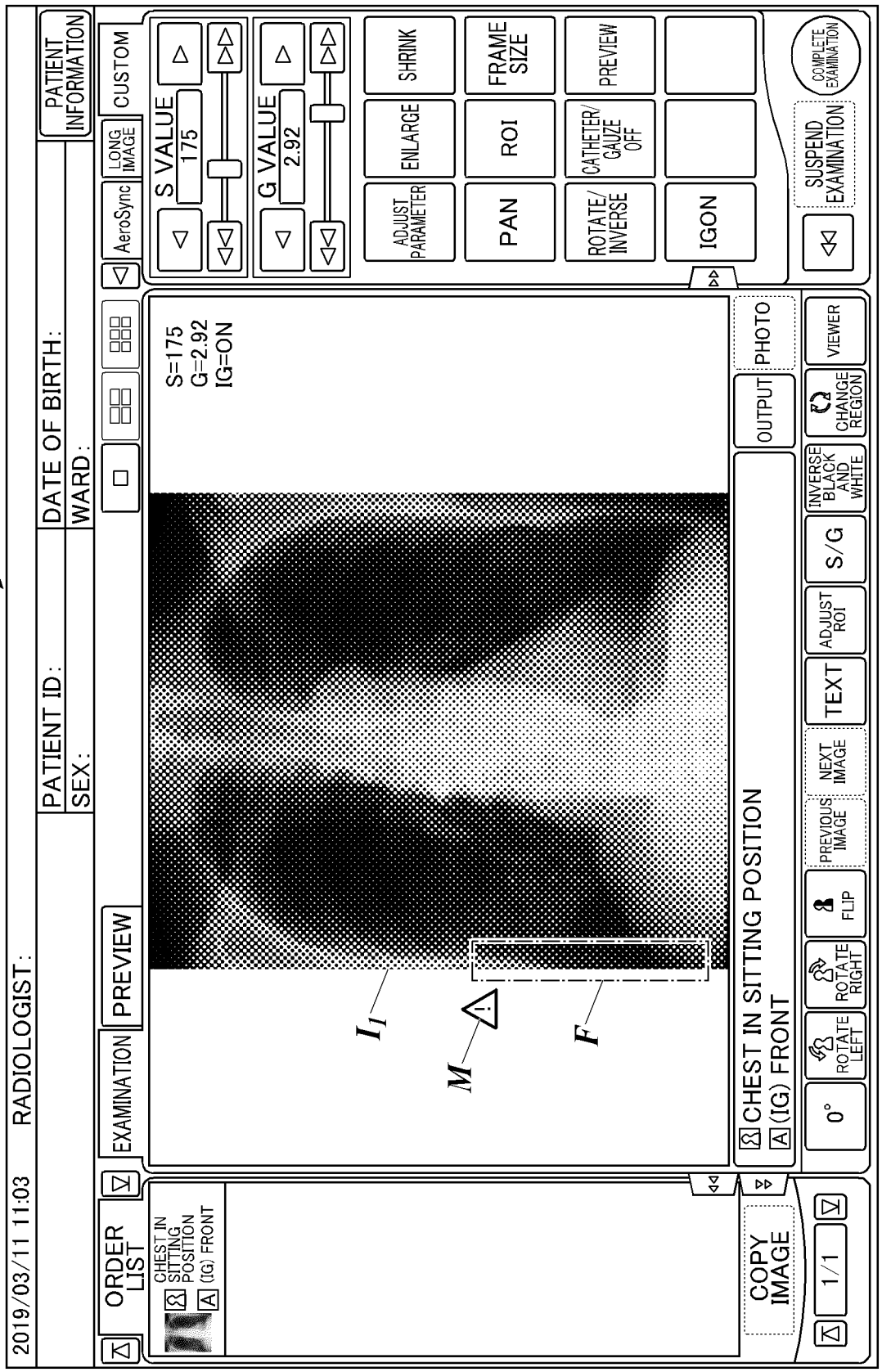
FIG. 5 is an example of a screen displayed on the display of the console in the first embodiment.

On the radiographic image $I_1$ being displayed, a region where the diagnosis target region is chipped or hidden may be circled with a frame F, or may have an attention mark M to attract the user, as shown in FIG. 5.

The detector figure $F_1$ is a rectangular frame the shape of which is similar to that of the radiation entrance plane of the radiation detector 2, as shown in FIG. 4.

The tubular-lamp figure $F_2$ is a circle and has a cross at its center that shows the center of irradiation.

The irradiated-field region R has the same shape as the detector figure $F_1$. FIG. 4 exemplifies a case where the irradiated-field region R and the detector figure $F_1$ perfectly coincide with one another. However, when the irradiated field deviates from the radiation entrance plane of the radiation detector 2 at the time of taking the radiographic image, the irradiated-field region R deviates from the detector figure $F_1$.

With the irradiated-field region R having a transparent color, the subject diagram $D_s$ is visible even when the irradiated-field region R is laid thereon.

FIG. 4 and so forth exemplify a case where the contour of the detector figure $F_1$ coincides with the contour of the radiographic image $I_1$. However, because the actual radiation detector 2 has a casing and a sensor substrate in the casing, an effective image region that generates charges when irradiated of the radiation detector is smaller than the contour of the casing.

In consideration of this, the detector figure $F_1$ may have double rectangular frames: an inner frame that is the frame shown in FIG. 4 and corresponds to the effective image region; and an outer frame (not shown) that surrounds the inner frame and corresponds to the casing.

When displaying the radiographic image $I_1$ and/or the position-reflected diagram $D_1$, the controller 41 in this embodiment displays a position display section C on the display 44. The position display section C indicates numerical values on relative positions of the radiation detector 2 and the radiation source 13 with respect to the subject S, and numerical values on the direction of the radiation source 13.

Further, the controller 41 in this embodiment displays position-change buttons B1, B2 that can be operated with touches or clicks on the display 44 (for example, on the right and left sides of the position display section C).

The controller 41 may output images, diagrams, and/or figures by sending data thereof to other apparatuses through the communication unit 42, instead of displaying them on the display 44. This also applies to an image output process in Step S7 to be described later.

After displaying the radiographic image $I_1$, the controller 41 determines whether or not a change input for simulating change of the position of the radiation detector 2 or the radiation source 13 has been performed (Step S5). In this embodiment, the controller 41 determines whether or not the position-change button B1 or B2 has been operated.

The controller 41 repeats the determination in Step S5 until the change input is performed.

When the user operates the position-change button B1 or B2 while the controller repeats the procedure in Step S5, the controller 41 determines that the change input has been performed (Step S5: YES), and performs an input receiving process to receive the change input.

The controller 41 functions as an input receiving unit by performing the input receiving process.

The controller 41 then changes the numerical values shown in the position display section C in response to the performed change input. More specifically, when the position-change button B1 on the left is operated for instruction to simulatively move the radiation detector 2 or the radiation source 13 to the right as viewed from the subject S (to the left in FIG. 4), the controller 41 reduces the corresponding numerical value in the position display section C. When the position-change button B2 on the right is operated for instruction to simulatively move the radiation detector 2 or the radiation source 13 to the left as viewed from the subject S (to the right in FIG. 4), the controller 41 increases the corresponding numerical value in the position display section C.

When the numerical values are smaller than zero (the radiation detector 2 or the radiation source 13 is moved from the initial position to the right as viewed from the subject S), the numerical value are shown in negative numbers.

After determining that the change input has been received (Step S5: YES), the controller 41 performs an image generation process (Step S6).

In the image generation process in Step S6, the controller 41 generates a simulation-reflected image $I_2$ that is an image of the subject reflecting the change of the position of at least one of the radiation detector 2 and the radiation source 13, on the basis of the detected positional relationships and the received change input.

More specifically, the controller 41 generates the simulation-reflected image $I_2$ by sliding pixel values of the radiographic image $I_1$ with respect to the image frame. That is, without being complemented, the simulation-reflected image $I_2$ would have a void region at the edge thereof opposite to the slide direction.

The controller 41 in this embodiment complements the void region using the model image stored in the storage 43. That is, the simulation-reflected image $I_2$ consists of a partial region $I_{11}$ being part of the radiographic image $I_1$ and a region $I_M$ being part of the model image and corresponding to the void region of the simulation-reflected image $I_2$.

Registration of the radiographic image $I_1$ and the model image may be performed with a method described in "Digital Subtraction Technique Between Temporally Sequential Chest Screening Images" in Konica Minolta technical report vol. 8, 1995, for example.

A three-dimensional radiographic image may be used as the model image. For example, a three-dimensional image is projected on a plane in a desired direction, and a two-dimensional image is obtained as the model image.

In the image generation process in Step S6, the controller 41 generates a changed position-reflected diagram $D_2$ in which the position of the figure $F_1$ and/or the figure $F_2$ is moved (i.e. the controller 41 adjusts the position-reflected diagram $D_1$) on the basis of the received change input.

The procedure to generate the changed position-reflected diagram $D_2$ is not required if the controller 41 has not output the position-reflected diagram $D_1$ in the image output process in Step S4.

The controller 41 functions as an image generation unit by performing the image generation process in Step S3 and the image generation process in Step S6.

After generating the simulation-reflected image $I_2$, the controller 41 performs the image output process again (Step S7).

In the image output process in Step S7, the controller 41 outputs the generated simulation-reflected image $I_2$.

Figure 6:
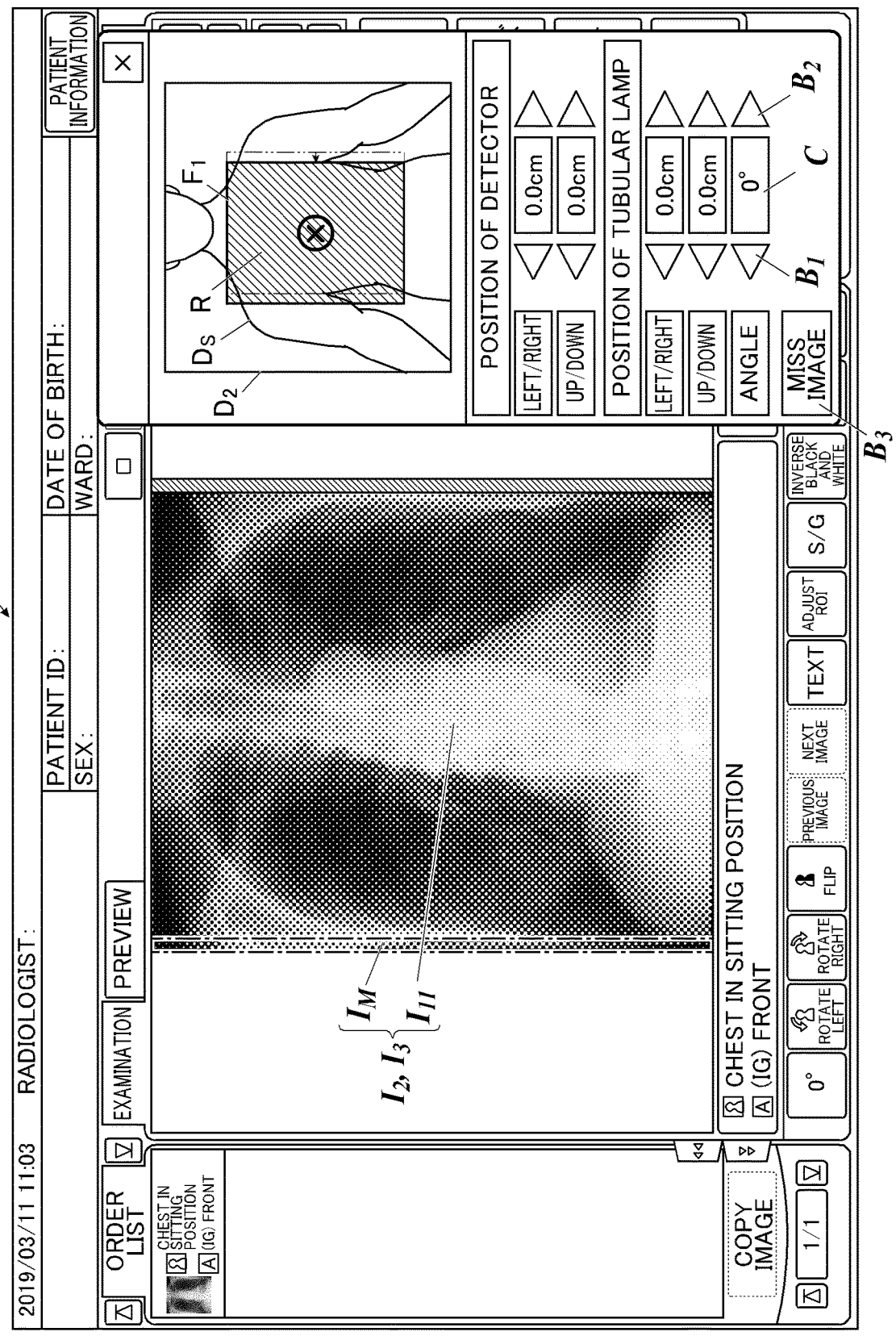
FIG. 6 is an example of a screen displayed on the display of the console in the first embodiment.

In this embodiment, the controller 41 displays the simulation-reflected image $I_2$ and the changed position-reflected diagram $D_2$ generated in the image generation process in Step S6 on the display 44, as exemplified in FIG. 6.

FIG. 6 exemplifies a case where the irradiated-field region R perfectly coincides with the detector figure $F_1$ (case where the position of the radiation detector 2 and the position and the angle of the radiation source 13 are simulatively adjusted at the same time by the same extent). However, when only either the change input for the radiation detector 2 or the change input for the radiation source 13 is performed in Step S5, the irradiated-field region R may deviate from the detector figure $F_1$.

In this embodiment, the controller 41 also displays numerical values indicating the simulative moving direction and the simulative moving distance of the radiation detector 2 and the radiation source 13 on the basis of the change input, and numerical values indicating the direction (angle) of the radiation source 13.

The controller 41 functions as an image output unit by performing the image output process in Step S4 and the image output process in Step S7.

After outputting the simulation-reflected image $I_2$, the controller 41 repeats the determination in Step S5.

During this time, on the basis of the simulation-reflected image $I_2$, the user determines whether or not the user can obtain a desired radiographic image by correcting the position of the radiation detector 2 and/or the radiation source 13 according to the numerical values indicated in the position display section C.

When the user determines that the user cannot obtain a desired radiological image by the correction according to the numerical values indicated in the position display section C and performs a change input with the position-change buttons B1, B2 again, the controller 41 generates a changed simulation-reflected image $I_3$ and the changed position-reflected diagram $D_2$ in accordance with the change input, and displays them on the display 44. That is, in response to the position-change buttons B1, B2 being operated, the detector figure $F_1$ and the tubular-lamp figure $F_2$ move on the subject diagram $D_s$ in the position-reflected diagram $D_1$, and the region shown in the changed simulation-reflected image $I_3$ shifts sequentially, as long as the display screen shown in FIG. 4 is displayed on the display 44.

With the simulation-reflected image $I_2$ and the changed position-reflected diagram $D_2$, the user can intuitively grasp how much and to which direction the radiation detector 2 and/or the radiation source 13 needs to be moved.

When the user determines that a desired radiological image can be obtained by the correction according to the numerical values indicated in the position display section C, the user does not need to further operate the position-change buttons B1, B2.

The numerical values indicated in the position display section C at this point serves as a method of correcting the position of the radiation detector 2 and/or the radiation source 13 (position correction method).

When the position correction method is determined, the user actually corrects the position of the radiation detector 2 and/or the radiation source 13 according to the position correction method.

After correcting the positions, the user retakes an image (s). When the radiographic image $I_1$ obtained in the image obtainment process in Step S1 is a pre-taken image, the user corrects the position of at least one of the radiation detector 2 and the radiation source 13 according to the displayed content, and takes a main image.

When the radiographic image $I_1$ obtained in the image obtainment process in Step S1 is a main image, the user treats the main image as a candidate miss image by, for example, pressing a miss-image button $B_3$ shown in FIG. 4, corrects the position of at least one of the radiation detector 2 and the radiation source 13, and retakes a main image.

A radiographic image taken at this stage is similar to the simulation-reflected image $I_2$. That is, the diagnosis target region shown in the radiographic image is not chipped or inclined.

As described above, the console 4 (positioning support apparatus) according to this embodiment simulates change in the positions of the radiation detector 2 and the radiation source 13 in accordance with a change input(s) performed so that the diagnosis target region in the simulation-reflected image $I_2$ is not chipped or inclined. When the diagnosis target region in the simulation-reflected image $I_2$ is no longer chipped or inclined, numerical values indicated in the position display section C at this point serve as a position correction method of how to correct the position of the radiation detector 2 and/or the radiation source 13 in order to take correct images.

Further, the simulation-reflected image $I_2$ displayed at this point shows a radiographic image to be obtained after the position of the radiation detector 2 and/or the radiation source 13 is corrected according to the position correction method.

Thus, according to the console 4 in this embodiment, when the position of the radiation detector 2 and/or the radiation source 13 deviates with respect to the position of the subject S, the user can easily learn how to correct the deviation and check whether or not the user can obtain a desired radiographic image by the correction.

Second Embodiment

Next, a second embodiment according to the present invention is described.

The same components as those in the first embodiment are denoted by the same reference numerals, and description thereof is omitted.

A console 4A in this embodiment is included in a radiographic imaging system 100A. Programs stored in a storage 43A of the console 4A are different from those stored in the storage 44 of the console 4 in the first embodiment.

Figure 7:
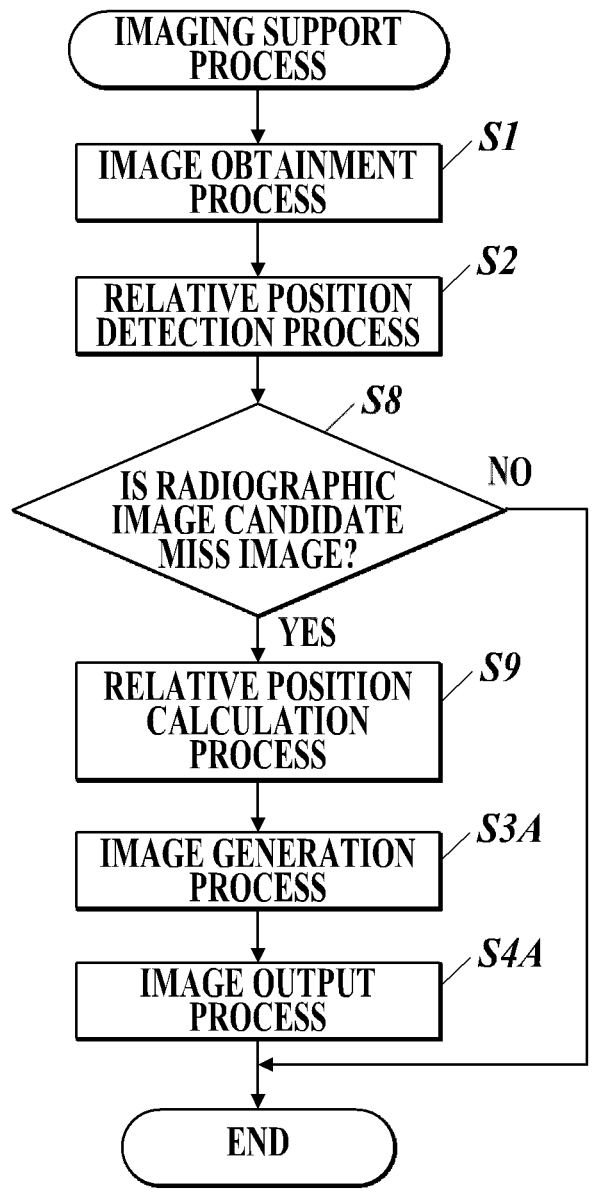
FIG. 7 is a flowchart showing an imaging support process performed by the console in a second embodiment.

More specifically, the controller 41 in this embodiment performs, after detecting the positional relationships in Step S2, an image determination process to determine whether or not an obtained radiographic image $I_1$ is a candidate miss image that does not meet conditions to be used for diagnosis (Step S8), as shown in FIG. 7.

A candidate miss image may be a main image or a pre-taken image. The method of determining whether or not the radiographic image $I_1$ is a candidate miss image is not specifically limited. The determination may be done on the basis of the detected positional relationships or a profile of signal values at the edge portions of the radiographic image $I_1$.

The controller 41 functions as an image determination unit by performing the image determination process in Step S8.

If the controller 41 determines in Step S8 that the obtained radiographic image $I_1$ is not a candidate miss image (Step S8; NO), the controller 41 ends the imaging support process because the positions of the radiation detector 2 and the radiation source 13 do not need to be corrected.

If the controller 41 determines in Step S8 that the obtained radiographic image $I_1$ is a candidate miss image (Step S8; YES), the controller 41 performs a relative position calculation process (Step S9).

In the relative position calculation process, the controller 41 calculates an appropriate positional relationship supposed to be appropriate between the subject and the radiation detector 2 and an appropriate positional relationship between the subject and the radiation source 13.

In this embodiment, the controller 41 calculates both the appropriate positional relationship between the subject and the radiation detector 2 and the appropriate positional relationship between the subject and the radiation source 13. However, only either of them may be calculated.

The controller 41 functions as a relative position calculation unit by performing the relative position calculation process in Step S9.

After calculating the appropriate positional relationships, the controller 41 performs an image generation process (Step S3A). In the image generation process in Step S3A, the controller 41 generates a simulation-reflected image $I_2$ that is an image of the subject S reflecting the change of the position of at least one of the radiation detector 2 and the radiation source 13, on the basis of the calculated appropriate positional relationships.

In the image generation process, the controller 41 lays, on the subject diagram $D_s$ in the position-reflected diagram $D_1$, a second detector figure $F_3$ (second figure) corresponding to the radiation detector 2 and a second tubular-lamp figure $F_4$ (second figure) corresponding to the radiation source 13. The second detector figure $F_3$ is laid such that a positional relationship between the subject diagram $D_s$ and the second detector figure $F_3$ is identical to the appropriate positional relationship between the subject S and the radiation detector 2. The second tubular-lamp figure $F_4$ is laid such that a positional relationship between the subject diagram $D_s$ and the second tubular-lamp figure $F_4$ is identical to the appropriate positional relationship between the subject S and the radiation source 13.

After generating the simulation-reflected image $I_2$ and the position-reflected diagram $D_1$, the controller 41 performs an image output process (Step S4A).

In the image output process in Step S4A, the controller 41 outputs the generated simulation-reflected image $I_2$.

Figure 8:
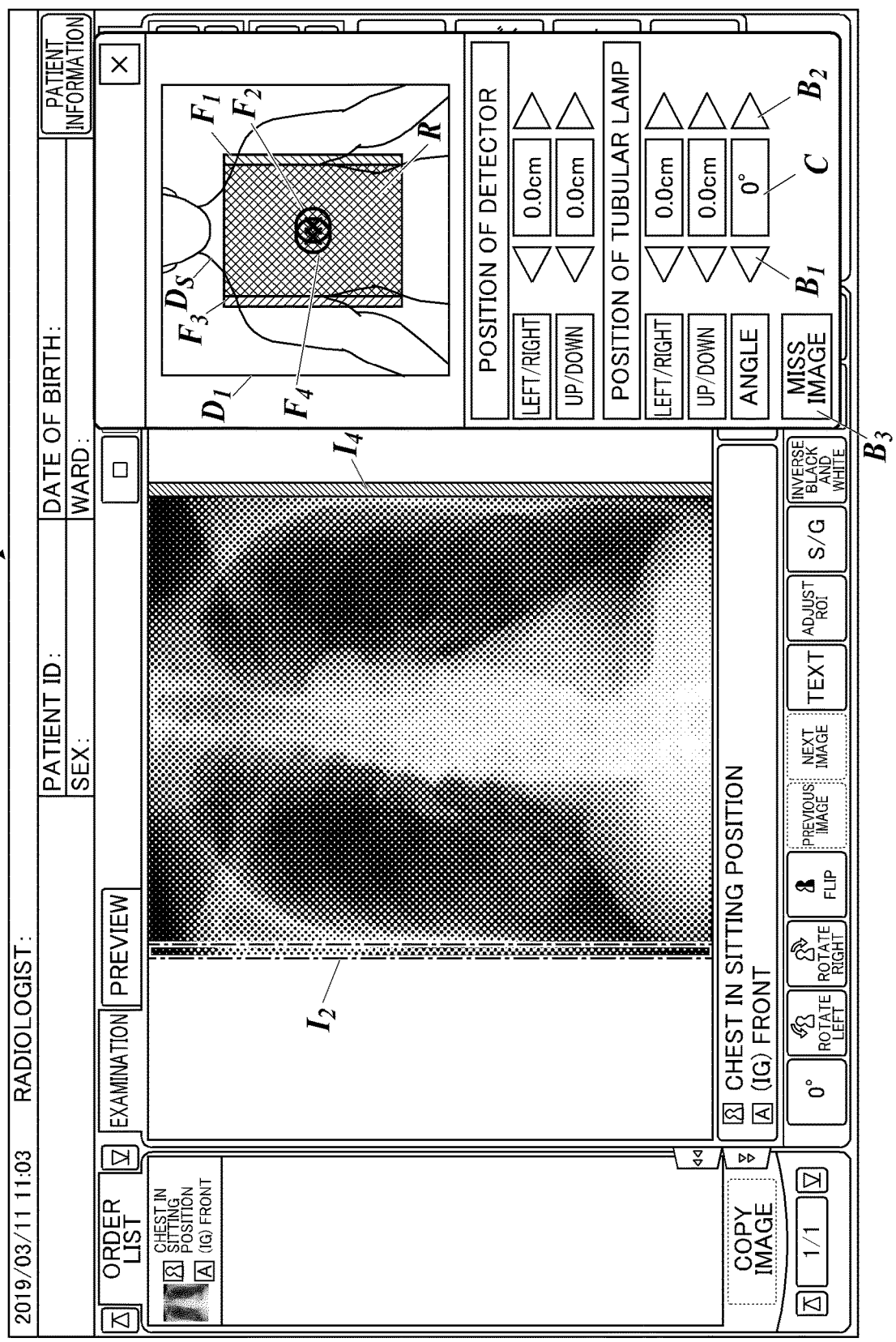
FIG. 8 is an example of a screen displayed on the display of the console in the second embodiment.

In this embodiment, as exemplified in FIG. 8, the controller 41 displays both the position-reflected diagram $D_1$ and the simulation-reflected image $I_2$ generated in the image generation process in Step S3A on the display 44.

When displaying the simulation-reflected image $I_2$, the controller 41 may also display an image $I_4$ that indicates a portion where part of the image of the subject has been shown in the radiographic image $I_1$, next to the simulation-reflected image $I_2$.

Further, the controller 41 may lay the detector figure $F_1$ and the tubular-lamp figure $F_2$ on the subject diagram $D_s$ on the basis of the positional relationships at the time of taking the radiographic image $I_1$, the positional relationships having been detected in Step S2 in this embodiment.

This makes it easier to recognize difference between the actual positional relationships at the time of taking the radiographic image $I_1$ and the appropriate positional relationships.

After displaying the simulation-reflected image $I_2$ and the position-reflected diagram $D_1$, the controller 41 ends the imaging support process.

Step S4A may be followed by Steps S5 to S7 of the imaging support process in the first embodiment so that the positions of the figures and the position correction method supposed to be appropriate and displayed by the console 4A can be adjusted.

As described above, according to the console 4A in this embodiment, when the position of the radiation detector 2 and/or the radiation source 13 deviates with respect to the position of the subject S, the user can easily learn how to correct the deviation and check whether or not a desired radiographic image can be obtained by the correction, as with the first embodiment.

Further, the console 4A automatically displays: the position correction method that is supposed to be appropriate; and the simulation-reflected image $I_2$ showing an image of the subject to be obtained after the position of the radiation detector 2 and/or the radiation source 13 is corrected according to the position correction method. Thus, the user can more easily learn the position correction method and determine whether or not a desired radiographic image can be obtained by the correction.

Although some embodiments of the present invention have been described, the present invention is not limited to the above-described embodiments and the like, and can be appropriately modified without departing from the scope of the present invention.

For example, the radiographic imaging systems 100 and 100A according to the above embodiments include the console 4 and the console 4A, respectively, each of which includes the display 44 on which the simulation-reflected image $I_2$ and the like are displayed and the operation unit 45 with which change inputs are received. However, means to display images and receive inputs in these systems are not limited to them. A portable terminal that includes a display and an operation unit and is capable of communicating with the console 4/4A may be used instead.

Further, in the radiographic imaging systems 100 and 100A according to the first and second embodiments, the user manually corrects the positions of the radiation detector 2 and the radiation source 13 according to the contents displayed by the console 4/4A. However, at least one of the radiation generator 1 and the imaging stand 3 may have a mechanism to move the radiation source 13 or the radiation detector 2 so that the position of the radiation source 13 or the radiation detector 2 is automatically corrected in accordance with change inputs received by the console 4.

Further, in the radiographic imaging systems 100 and 100A according to the first and second embodiments, after the position correction method is determined, the controller 41 may send the position correction method and the obtained radiographic image $I_1$ to a server (e.g., the PACS) having a data base, and cause the server to store the position correction method and the radiographic image $I_1$.

Thus, the user can call the radiological image $I_1$ and the position correction method from the database and use them for analyzing factors of candidate miss images or the like at a later date.

Further, the above description discloses an example of using a hard disk, a nonvolatile semiconductor memory, or the like as the computer-readable medium storing the program according to the present invention. However, the present invention is not limited to this example. For example, as other computer-readable recording media, a portable recording medium, such as a CD-ROM, can be used. Also, a carrier wave can be used as a medium that provides data of the program of the present invention through communication lines.

The detailed configuration and the detailed operation of the devices/components included in the radiographic imaging system can be appropriately modified within the scope of the present invention.

Although embodiments of the present invention have been described and illustrated in detail, the disclosed embodiments are made for purposes of illustration and example only and not limitation. The scope of the present invention should be interpreted by terms of the appended claims

What is claimed is:

1. A positioning support apparatus comprising a hardware processor that:
   obtains a radiographic image of a subject taken through a radiography;
   based on the obtained radiographic image, detects a relative positional relationship between the subject and at least one of a radiation detector and a radiation source, the positional relationship being at a time when the radiographic image is taken;
   receives a change input for simulating a change of a position of the at least one of the radiation detector and the radiation source;
   based on the detected positional relationship and the received change input, generates a simulation-reflected image that is an image of the subject reflecting the change of the position of the at least one of the radiation detector and the radiation source; and
   outputs the generated simulation-reflected image.

2. The positioning support apparatus according to claim 1, wherein the hardware processor
   generates a position-reflected diagram by laying, on a subject diagram showing at least a part corresponding to an imaging target part imaged in the radiographic image, a first figure corresponding to the at least one of the radiation detector and the radiation source such that a positional relationship between the subject diagram and the first figure is identical to the detected positional relationship between the subject and the at least one of the radiation detector and the radiation source, and
   outputs the position-reflected diagram and the radiographic image.

3. The positioning support apparatus according to claim 2, wherein the hardware processor generates a changed position-reflected diagram in which a position of the first figure is moved, based on the received change input, and
   outputs the changed position-reflected diagram and the simulation-reflected image.

4. The positioning support apparatus according to claim 3, wherein the hardware processor
determines whether or not the obtained radiographic image is a candidate miss image that does not meet a condition for a diagnosis,
in response to determining that the radiographic image is the candidate miss image, calculates an appropriate positional relationship that is supposed to be appropriate between the subject and the at least one of the radiation detector and the radiation source, and
based on the calculated appropriate positional relationship, lays, on the subject diagram included in the position-reflected diagram, a second figure corresponding to the at least one of the radiation detector and the radiation source such that a positional relationship between the subject diagram and the second figure is identical to the appropriate positional relationship.

5. A radiographic imaging system comprising:
a radiation detector that generates a radiographic image of a subject based on a radiation received from a radiation source;
a hardware processor that:
   detects, based on the radiographic image generated by the radiation detector, a relative positional relationship between the subject and at least one of the radiation detector and the radiation source, the positional relationship being at a time when the radiographic image is taken,
   receives a change input for simulating a change of a position of the at least one of the radiation detector and the radiation source,
   based on the detected positional relationship and the received change input, generates a simulation-reflected image that is an image of the subject reflecting the change of the position of the at least one of the radiation detector and the radiation source; and
a display that displays the generated simulation-reflected image.

6. A non-transitory computer-readable storage medium storing a program that causes a computer to perform:
   image obtaining that is obtaining a radiographic image of a subject taken through a radiography;
   relative position detecting that is detecting, based on the radiographic image obtained in the image obtaining, a relative positional relationship between the subject and at least one of a radiation detector and a radiation source, the positional relationship being at a time when the radiographic image is taken;
   input receiving that is receiving a change input for simulating a change of a position of the at least one of the radiation detector and the radiation source;
   image generating that is generating, based on the positional relationship detected in the relative position detecting and the change input received in the input receiving, a simulation-reflected image that is an image of the subject reflecting the change of the position of the at least one of the radiation detector and the radiation source; and
   image outputting that is outputting the simulation-reflected image generated in the image generating.

* * * * *